(12) United States Patent
Sakamoto et al.

(10) Patent No.: US 6,522,405 B2
(45) Date of Patent: Feb. 18, 2003

(54) METHOD AND APPARATUS FOR MONITORING SUB-MICRON PARTICLES

(75) Inventors: Akira Sakamoto, Osaka (JP); Yasuhiro Hayashi, Osaka (JP); Yoshihisa Yamashita, Osaka (JP); Koji Yamamoto, Osaka (JP)

(73) Assignee: Mikunikikaj Co. Ltd., Osaka (JP)

( * ) Notice: Subject to any disclaimer, the term of this patent is extended or adjusted under 35 U.S.C. 154(b) by 0 days.

(21) Appl. No.: 09/935,174

(22) Filed: Aug. 23, 2001

(65) Prior Publication Data

US 2002/0044281 A1 Apr. 18, 2002

(30) Foreign Application Priority Data

Aug. 23, 2000 (JP) ........................................ 2000-253090

(51) Int. Cl.[7] ........................... G01N 15/02; G01N 21/00
(52) U.S. Cl. .......................... 356/336; 356/337; 356/338
(58) Field of Search ................................. 356/336, 337, 356/338, 343, 335; 250/574

(56) References Cited

U.S. PATENT DOCUMENTS 3,941,479 A * 3/1976 Whitehead .................. 356/102
5,534,999 A * 7/1996 Koshizuka et al. .......... 356/338

* cited by examiner

Primary Examiner—Frank G. Font
Assistant Examiner—Roy M. Punnoose
(74) Attorney, Agent, or Firm—Blank Rome Comisky & McCauley, LLP

(57) ABSTRACT

Amount of sub-micron particles in fluid such as ultra pure water classified each range of particle dimensions are detected by a simple apparatus in which a light beam from a coherent light source(1) is converged (2) in such a manner that the light beam is focused in a stream (3) of particle-containing fluid, the light passed through the stream and diffracted by the particles is received by a photo-detector (4) which is positioned at an opposite side of the coherent light source with respect to the stream and substantially on an optical axis of the light beam, so that the number of particles in the stream is distinguished into plural ranges according to each frequencies of the signals emitted from the photo-detector and counting each numbers of the particles contained the ranges.

8 Claims, 2 Drawing Sheets

Sample Fluid

Intensity of Light

METHOD AND APPARATUS FOR MONITORING SUB-MICRON PARTICLES

BACKGROUND OF THE INVENTION

1. Field of the Invention

The present invention relates to a method and apparatus for monitoring or detecting amount of sub-micron particles every range of their dimensions.

The method according to the present invention is advantageously applicable to monitor and control impurity particles in fluid such as pure water and ultra pure water used in electronics industries, biotechnology, medical and pharmaceutical application and food industries. The method of the present invention can be used to evaluate the performance of separation membranes and filtration system.

2. Related Arts

The conventional method for monitoring or detecting particles in fluids are classified into following four categories;

(1) Shadow system in which decrement of light intensity caused by traveling particles in fluid passing across an optical axis of parallel ray.

(2) Microscope system in which fine particles in fluid are caught by a membrane filter or the like and are observed or counted by a electron scanning microscope.

(3) Light scattering in which fluid is irradiated with an intensive light such as a laser beam and the resulting scattered light is collected by a lens so that the focused light is detected by a photo-multiplier.

(4) Imaging system in which a fluid is irradiated with a light and the resulting contrast of light is detected by a photo-diode alley and an image of particles in the fluid id formed by a computer.

New techniques such as ultrasonic scattering techniques are also proposed.

In the case of the shadow system (1), however, direction of fine particles in limited to particle size of about 1 $\mu$m and hence this detection system can not be used for sub-micron particles. In the microscope system (2), more than half day is required to obtain the result.

The light scattering system (3) is the main current of development in particle counters or detectors and now ultra-fine particles having the particle size of less than 0.07 $\mu$m can be detected by using a light source having shorter wave length such as argon laser. In fact, Japanese patent laid-open No. 4-39,635 discloses a technique to determine the precise number of fine containment particles each having the particle size of lower than 0.07 $\mu$m contained in ultra pure water. This patent proposes to use two detectors each receive the scattered light so that a particle counter produces a signal when two detectors detect the scattered light simultaneously. This system, however, requires a high-power laser as well as very sensitive photo-multiplier, resulting in a large costly system. Still more, in this system, precise alignment between an axis of fluid stream containing particles to be detected and an optical axis is required in order to assure the reliability of measurement. Japanese patent laid-open No. 62-803 discloses an automated apparatus that facilitates this alignment.

Japanese patent laid-open No. 63-19535 discloses a variation of the imaging system (4). In this patent, a laser beam impinges vertically to a flow of sample fluid and the diffracted and scattered light is passed through a Fourier-transformation optical system or a lens to produce a Fraunhofer diffraction image that is treated in order to evaluate fine particles in the fluid. In this patent, a diameter of a laser beam is enlarged to obtain a parallel ray that is directed to the sample fluid. This system requires a complicated computer system.

Then, for the above situation, we proposed a new method and apparatus for monitoring and detecting fine particles of sub-micron as contaminant in fluid by a simple and very economical apparatus as U.S. Pat. No. 5,534,999.

The above patent provides a method comprising converging a light beam from a coherent light source so that the resulting focused light passes through a stream of fluid containing particles therein in such a manner than a focus of the focused light is located in the stream of fluid, receiving a light passed through the stream of fluid and diffracted by the particles by a photo-detector which is positioned at an opposite side of the coherent light source with respect to the stream and on an optical axis of the light beam to produce electrical signals, and counting numbers of particles in the stream by treating the electrical signals.

The above patent provides also an apparatus comprising a coherent light source, an optical system for converging a light beam emitted out of the coherent light source to produce a converged light, a cell through which a stream of fluid containing particles is flown and being located in the neighborhood of a focus of the converged light beam, a photo-detector which is positioned at an opposite side of the coherent light source with respect to the stream and on an optical axis of the light beam to produce electrical signals, and an electric circuit for counting numbers of particles in the stream by treating the electrical signals.

The above method is based on such surprising and unexpected finding that the existence of sub-micron particles in a fluid stream can be detected or monitoring by utilizing diffraction phenomenon of a transmitted light, which is observed when a converged coherence light is focused on the light stream. In fact, it is not known to use the transmitted light of a converged light directly for detecting fine particle before the invention according to the patent.

In the method according to the above invention, the diffracted image can be obtained for a particle whose particle size is smaller than 0.1 $\mu$m that is not observable in known techniques. Of course, particles having the particle size of bigger than 1.0 $\mu$m also can be detectable with high sensitivity by the method according to the method.

In the conventional detection technique, dispersed particles are irradiated with an illumination parallel ray so that the resulting transmitted light image is Fourier-transformed as is described in the Japanese patent laid-open No. 63-19, 535.

The detection principle of the method according to the present invention is different from those of known methods but the theory why the particles in fluid is detected precisely by the method according to the present invention can not be explained completely at this stage. Following is one of probable explanations.

By the way, the method and apparatus according to our patent can detect only amount of all particles existing in the fluid, but can not detect dimensions of the particles. Therefore, an object of the present invention is to provide an improved method and apparatus that permits to detect particles every range of dimensions of the particles.

SUMMARY OF THE INVENTION

As explained before, the method and the apparatus according to the invention disclosed in U.S. Pat. No. 5,534, 999 permit detect an existence of very small particles fluid. Furthermore, according to the method and apparatus of the present invention, dimension of the particles can be detected.

In the method and the apparatus according to the invention disclosed in U.S. Pat. No. 5,534,999, the particles pass through the converged laser beam. Therefore, each passing time of the particle is different from each other corresponding to distance from the focal point of the converged light beam.

Namely, length of a passage of particles passing near by the focal point is very short. Length of a passage of the particles passing far from the focal point is very long. On the other hand, all the particle moves by equal velocity. Therefore, the photo-detector emits short signals corresponding to the particles passing near by the focal point, and the photo-detector emits a long signal corresponding to the particles passing far from the focal point. In other words, the signal frequency corresponds to the distance between the passage of the particles and the focal point.

At the same time, as explained before, small particles can be detected only passing near to the focal point. Therefore, low frequency signal emitted from the photo-detector corresponds to only large particles and high frequency signal emitted from the photo-detector corresponds to all particles.

Physical phenomenon mentioned above can be utilized for every range of dimension of the particle by electrically treating the signals emitted from the photo-detector.

Now, the present invention will be described with referring to drawings but the present invention should not be limited to an embodiment shown in the drawings.

DESCRIPTION OF THE PREFERRED EMBODIMENT

Figure 1:
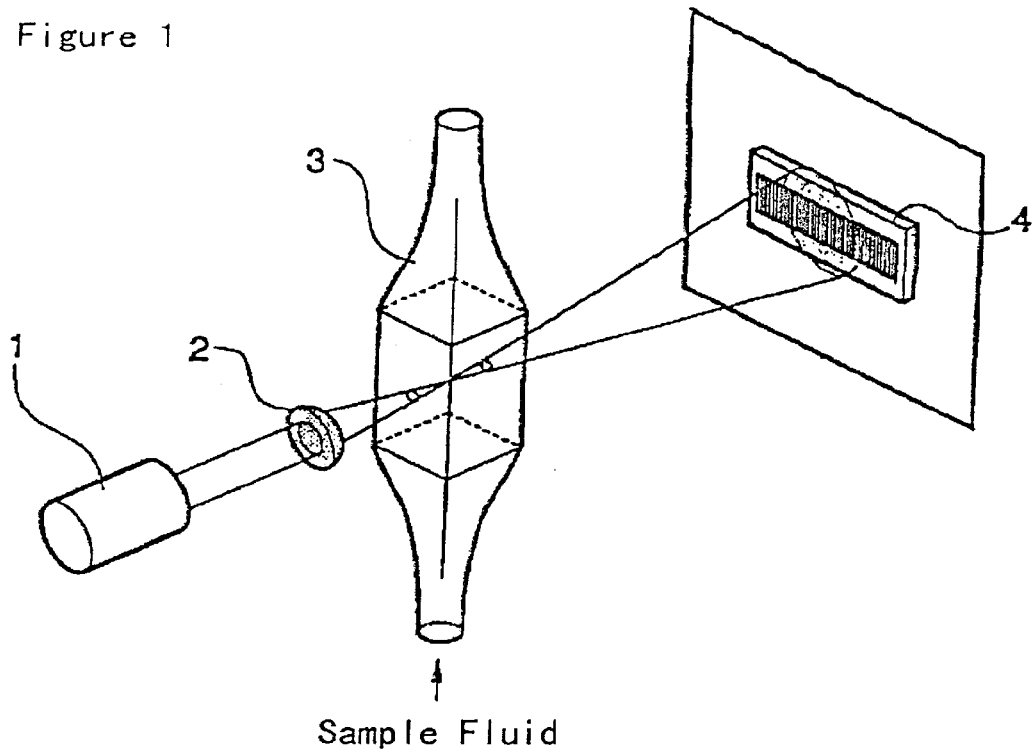
FIG. 1 is a perspective view illustrating fundamental construction of an apparatus to carry out the method according to the present invention.

As shown in FIG. 1, an apparatus to carry out the method according to the present invention comprises a laser (1) as a coherent light source, an optical system, preferably a lens (2) for converging a light beam emitted out of the coherent light source to produce a covered light, a cell (3) through which a stream of fluid containing particles is flown, which is located in the neighborhood of a focus of the converged light beam, a photo-detector (4) which is positioned at an opposite side of the coherent light source (1) with respect to the stream and substantially on an optical axis of the light beam such as a photo-diode or a photo-diode alley, and an electric circuit (not shown in FIG. 1) for converting the resulting light intensity signals or a defecation image detected by the photo-detector (4) to electrical signals from which numbers of particles in the stream is counted. All elements used in the present invention are available on market and very cheap.

Figure 2:
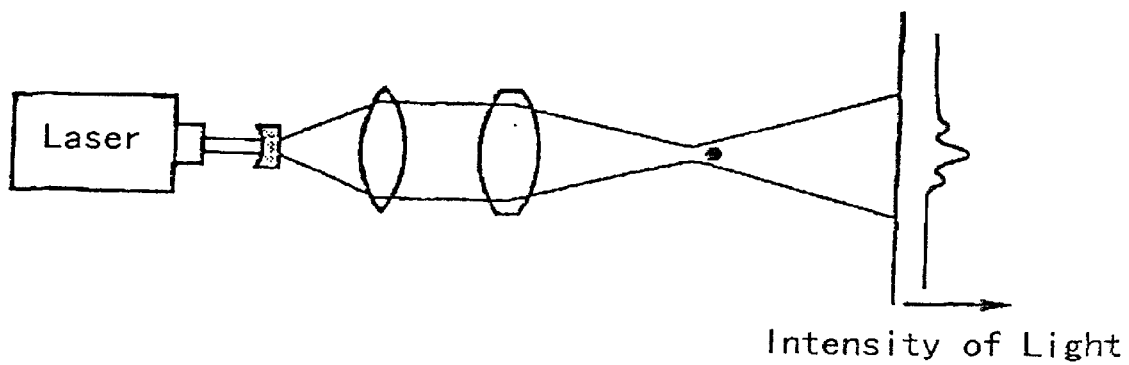
FIG. 2 is an illustration for explaining the principle to detect an existing particles in the method according to the present invention.

The coherent light source may consist of a laser (1) and a collimator lens system (shown in FIG. 2). The laser (1) can be any laser but is preferably a laser diode or semiconductor laser of small power. In other words, a cheap laser diode can be used advantageously in the method according to the present invention. Sensitivity increases with decrement of wave length of laser oscillation. Inventors confirmed that the detection principle of the present invention can be applicable for a laser diode whose power is smaller than 1 mW, for example 0.2 mW.

The focal distance of the optical system or lens (2) for converging a light beam is determined in function of the particle size to be detected. For example, a lens having the focal distance f=10 mm may be used to detecting a fine particle whose particle size is 0.2 μm.

The cell (3) must be transparent at least on light-receiving face and light existing face but can have a very simple structure because no consideration is required to stray light. The cell (3) has not necessarily a rectangular section as shown in FIG. 1 but can have any section. The cell (3) can be a separate piece from a tube for a stream of fluid containing particles but, according to another advantage of the present invention, is preferably a part of transparent tube through which the stream of fluid containing particles is flown. The transparent tube can be made of fluoro resin in order to resist chemicals.

In practice, a suitable adjusting mechanism is preferably used for positioning the optical system (2) so that the focused beam is focuses in the neighborhood of the center of the cell (3).

Not so high sensitivity is required in the photo-detector (4) if the photo-detector (4) can detect the diffraction image hidden in the transmitted light. In this sense, photo-diode can be used. The photo-detector (4) can be comprise a single photo-diode but preferably consitutes of a photo-diode alley. The photo-diode alley is preferably arranged perpendicularly to the direction of the stream and also perpendicularly to the optical axis.

The diffraction image or the distribution of intensity of a converged light observed in the photo-detector (4) used in the apparatus according to the present invention is illustrated at the right side of FIG. 2.

In Practice, signals from elements in the photo-detector alley are multiplied in differential amplifiers to improve the SN ratio of the photo-detector (4) in such a manner that an electric signal of zero is produced when the elements in the photo-detector alley are irradiated uniformly or no particle passes through the cell (3), while suitable electric signal that represents characteristics (number, size etc.) of the particles is produced when any change in intensity caused by the diffraction image of a converged light is appeared in the elements in the photo-detector alley.

Furthermore, dimension of particles can be distinguished by the method and the apparatus according to the present invention.

Figure 3:
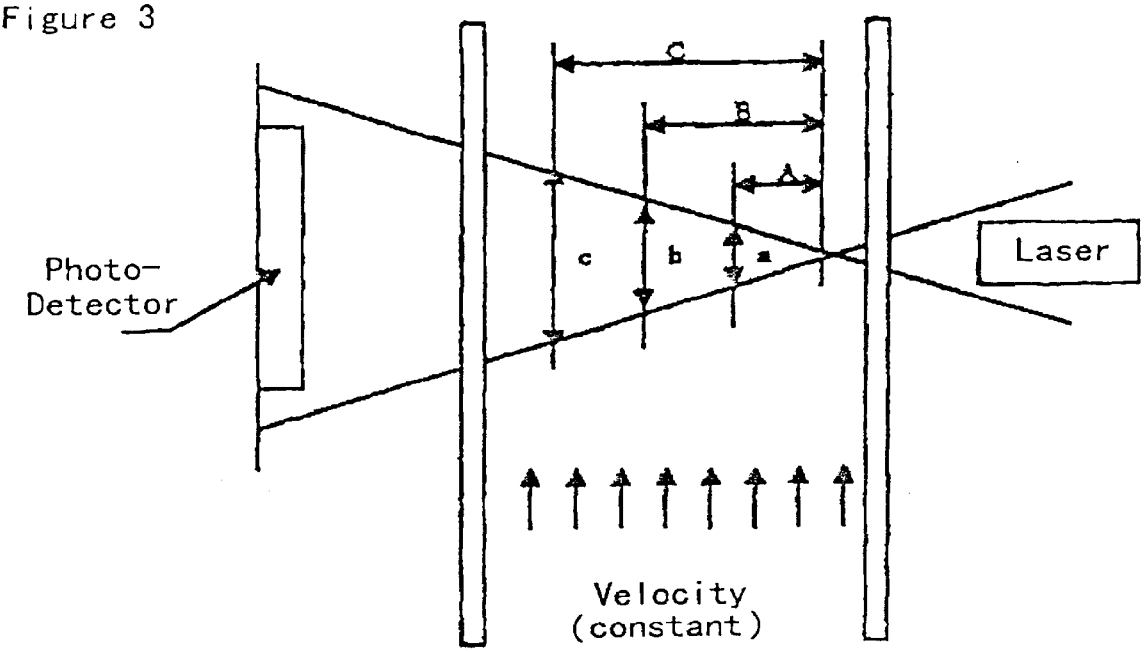
FIG. 3 is an illustration for explaining the principle to distinguished into plural ranges according to each frequency the method according to the present invention.

As shown in FIG. 3, the particles pass through the converged laser beam. Therefore, each passing time of the particle is different from each other corresponding to distance from the focal point of the laser beam.

Namely, length of a passage (1) of particles passing near by the focal point is very short corresponding to its distance (A) from the focal point. Length of a passage (c) of the particles passing far from the focal point is very long corresponding to its distance (C) from the focal point. And, length of a passage (b) of the particle passing between passage (a) and passage (c) is middle.

All the particles moves by equal velocity. Therefore, the photo-detector emits a short signal corresponding to the particles passing the passage (a), and the photo-detector emits a long signal corresponding to the particles passing the passage (c). In other words, the signal frequency corresponding to the particles passing the passage (a) becomes high and the signal frequency corresponding to the particles passing the passage (c) becomes low.

At the same time, as explained before, small particles can be detected only near to the focal point. Therefore, low frequency signal emitted from the photo-detector corresponds to only large particles and high frequency signal emitted from the photo-detector corresponds to all particles.

Physical phenomenon mentioned above can be utilized for every range of dimension of the particles by electrically treating the signals emitted from the photo-detector.

Figure 4:
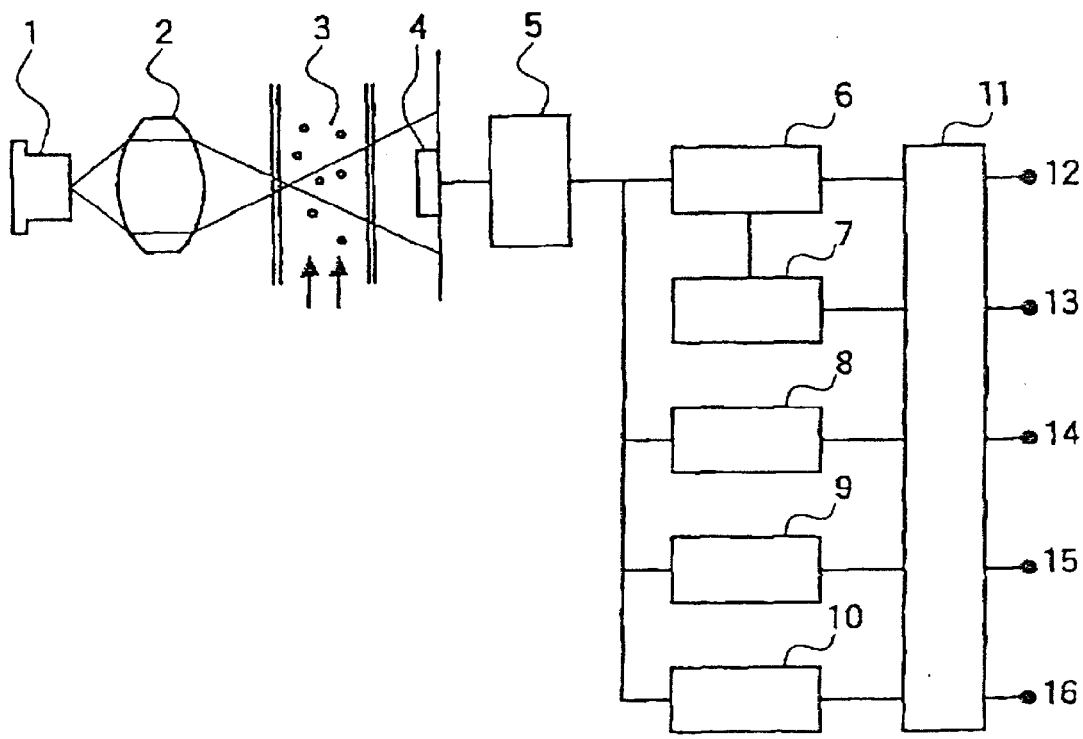
FIG. 4 is a block chart illustrating fundamental construction of an electric circuit to treat electric signals in the apparatus according to the present invention.

FIG. 4 shows a construction of a circuit to treat the signals emitted from the photo-detector corresponding to the particles having various dimensions.

The circuit shown in the FIG. 4 comprises an amplifier 5, a wave form transformer 6, a voltage-frequency conversion circuitry 7, a lowpass filter 8, a bandpass filter 9, a high pass filter 10 and a rectangular signal shaper 11.

The amplifier 5 receives output signal of the photo detector 4. The waveform transformer 6 receives the output signal of the amplifier 5 and shapes its waveform. The voltage-frequency conversion circuitry 7 receives the output signal of the waveform transformation circuitry 6. The lowpass filter 8, bandpass filter 9 and high pass filter 10 receive the output signal of the amplifier 5. And, the output signals of the waveform transformer 6, the voltage-frequency conversion circuitry 7, the lowpass filter 8, the bandpass filter 9 and the high pass filter circuitry 10 are connected to terminals 12–16 through rectangular signal shaper 11.

As explained before, the output signal of the amplifier 5 is corresponds to the Sub-micron particles contained in the fluid entirely. The waveform transformer 6 outputs turbidity signals to terminal 12 when a density of the particle is low. The voltage-frequency conversion circuitry 7 outputs turbidity signals to terminal 13 when a density of the particle is high. This output signals are based on a method explained in Japanese patent laid-open No. 4-56418 (corresponding to U.S. Pat. No. 5,534,999).

On the other hand, each filter 8, 9 or 10 lets pass only a signal of specified range of frequency. As explained before, the frequencies of the signals correspond to the distance between the passage of the particles and the focal point. Therefore, the output signal from the lowpass filter 8 corresponds to the bid Sub-micron particle detected in the era far from the focal point. The output signals from the high pass filter 10 is correspond to all the sub-micron particles which passed near by the focal point. By same principal, the output signal from the bandpass filter 9 corresponds to the Sub-micron particles having average dimension.

After all, the output signals from each filters 8, 9 and 10 are converted into pulse signals by the rectangular signal shaper 11 and emitted as values corresponding to the amount of the particles contained in the fluid every range of dimension of the particles.

EXAMPLE

We prepared a sample fluid which contained Sub-micron particles having different size and detected the particles by using the apparatus shown in FIG. 1 and FIG. 4 under following condition shown in Table 1.

TABLE 1

Coherent light source (Laser diode);
   Wave length: 685 nm
   Output power: 2 mW
Optical cell;
   Bore: 4 [mm]
   Materials: Fusion quartz glass tube (mirror surface finishing)
Photo-detector: Photo diode (1 × 7 mm)
Sample fluid;
   Fluid materials: extra pure water
   Flow velocity in thc cell: 50 [mm/second]
The particle dispersed in the fluid;
   Materials: Polystyrene stem polymer
   Particle size (CV value): less than 3% (a catalogue value)
   A diameter of a particle: 0.506, 1.001, 1.418 [$\mu$m]
   Mixing ratio of the particles: 1:2:3

Value (relative value) of pulse signal output from the filter circuit 14, 15 and 16 is shown in table 2.

TABLE 2

Output from filter circuit 14:5
(corresponding to amount of big particles)
Output from filter circuit 15:7
(corresponding to total amount of small and middle)
Output from filter circuit 16:4
(corresponding to amount of all particles)

The values mentioned above were multiplied by each area corresponding to section of the light beam which the each size particle passed through. Account results are shown in Table 3.

TABLE 3

Value corresponding to number of big particles: 1.15
Value corresponding to number of small and middle particles: 2.38
Value corresponding to all particles: 4.00

As shown in the table 3, the ratio of each output signal is almost "1:2:3". It is identified that he method according to the present invention is effective. Actually, it is preferred to calibrate equipment beforehand by using a sample fluid so that accuracy of the measurement is improved.

What is claimed is:

1. A method for detecting particles comprising converging a light beam from a coherent light source so that the resulting focused light passes through a stream of fluid containing particles therein in such a manner that a focus of the focused light is located in the stream of fluid, receiving a light passed through the stream of fluid and diffracted by the particles by a photo-detector which is positioned at an opposite side of the coherent light source with respect to the stream and on an optical axis of the light beam to produce electrical signals, and counting numbers of particles in the stream by treating the electrical signal;

wherein the electrical signals have frequencies dependent on a size of each particle and a distance of each particle from the focus and in that the electrical signals are distinguished into plural ranges according to the frequency of each of the signals and counting each number of the particles contained the ranges by treating the electrical signals.

2. The method set forth in claim 1 wherein said coherent light source is a laser diode.

3. The method set forth in claim 1 wherein said photo-detector comprises a photo-diode-alley.

4. The method set forth in claim 1 wherein said fluid is pure water or ultra pure water.

5. An apparatus for detecting particles comprising a coherent light source, an optical system for converging a light beam emitted out of the coherent light source to produce a converged light, a cell through which a stream of fluid containing particles is flown and being located in the neighborhood of a focus of the converged light beam, a photo-detector which is positioned at an opposite side of the coherent light source will respect to the stream and on an optical axis of the light beam to produce electrical signals, and an electric circuit for counting numbers of particles in the stream by treating the electrical signals;

wherein the electrical signals have frequencies dependent on a size of each particle and a distance of each particle from the focus and in that the apparatus further comprises a lowpass filter, highpass filter and/or bandpass filter so that the electrical signals are distinguished into plural ranges according to the frequency of each of the signals, and in that the electric circuit comprises a circuit for counting each number of the particles contained in the ranges by treating the electrical signals.

6. The apparatus set forth in claim 5 wherein said coherent light source is a laser diode.

7. The apparatus set forth in claim 5 wherein said photo-detector comprises a photo-diode-alley.

8. The apparatus set forth in claim 5 wherein said fluid is pure water or ultra pure water.

* * * * *